United States Patent [19]
Onik

[11] Patent Number: 5,584,855
[45] Date of Patent: Dec. 17, 1996

[54] SAFETY SURGICAL GRASPING FORCEPS

[76] Inventor: Gary M. Onik, 8129 Sand Pointe Blvd., Orlando, Fla. 32803

[21] Appl. No.: 430,890

[22] Filed: Apr. 27, 1995

[51] Int. Cl.⁶ ................................................ A61B 17/28
[52] U.S. Cl. ........................ 606/207; 606/205; 606/206
[58] Field of Search .................................. 606/205, 206, 606/207, 51, 52, 79, 167, 170; 128/751, 752, 753, 754, 755

[56] References Cited

U.S. PATENT DOCUMENTS

| | | | |
|---|---|---|---|
| 5,308,358 | 5/1994 | Bond et al. | 606/207 |
| 5,394,885 | 3/1995 | Francese | 606/207 |

*Primary Examiner*—Michael Powell Buiz
*Assistant Examiner*—Kevin Truong
*Attorney, Agent, or Firm*—Connolly & Hutz

[57] ABSTRACT

A grasping forceps in the form of a rongeur having the teeth of its jaws displaced inwardly to create a rim between the outer edge of each jaw and its teeth which acts as a barrier for pushing the dura or tissue away from the teeth during the closing of the jaws. In other embodiments the barrier may take the form of guide members such as springs mounted to each jaw. In one such embodiment the guide members may comprise a guide member interconnecting the jaws at their distal end with guide members also interconnecting the jaws on each side of the jaws inwardly of the distal end. In a further variation each guide member may be mounted to a respective jaw peripherally around and outwardly of the jaw.

14 Claims, 2 Drawing Sheets

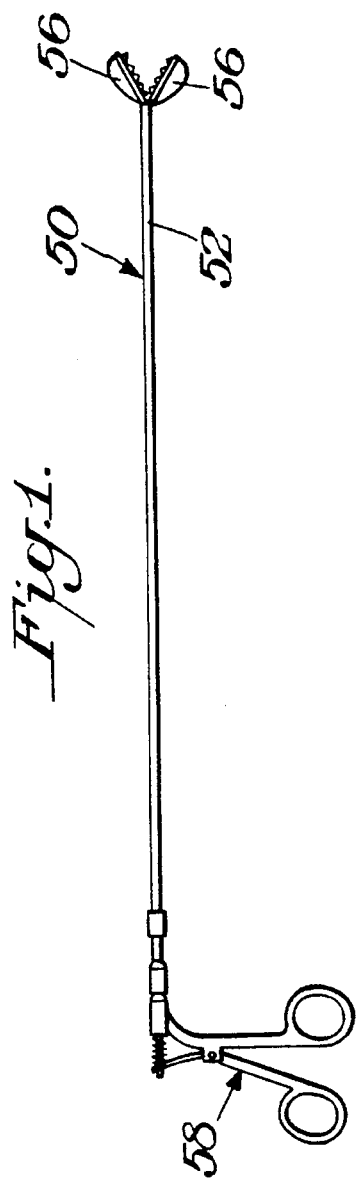
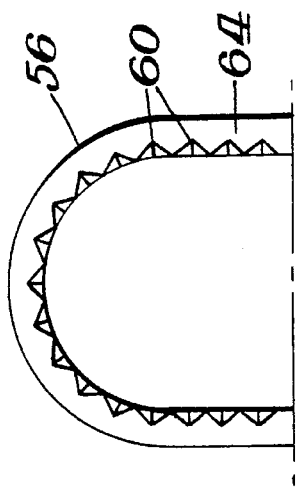
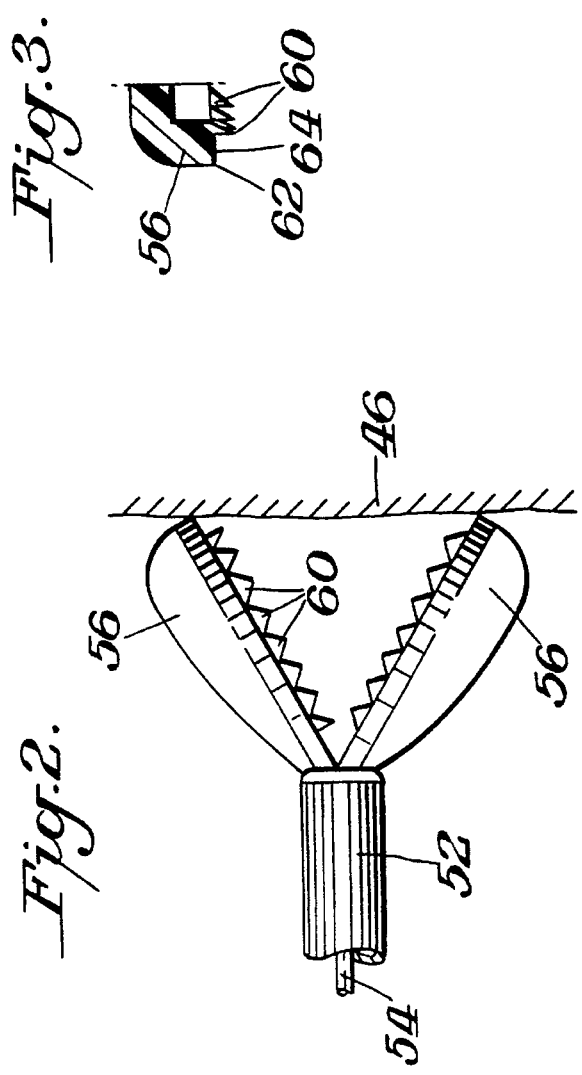

SAFETY SURGICAL GRASPING FORCEPS

BACKGROUND OF THE INVENTION

Surgical instruments such as discectomy devices have been used for various purposes such as removing nucleus pulposus from a herniated spinal disc. These devices include various forms of grasping forceps. One form of grasping forceps is a rongeur which includes a pair of movable jaws having teeth for capturing the disc material between the jaws and then closing the jaws to confine the disc material so that it can be removed when the rongeur is withdrawn from the operative site.

A disadvantage with conventional grasping forceps, such as rongeurs, is the possibility of the jaws clamping against the dura or a major blood vessel whereby the structure is injured by the closing teeth.

SUMMARY OF THE INVENTION

An object of this invention is to provide a safety grasping forceps which minimizes the likelihood that the dura or other tissue not intended to be removed would enter the jaws and be damaged.

A further object of this invention is to provide a device in the form of a rongeur which contains structure for moving the dura or vessel out of the operative area.

In accordance with one embodiment of this invention the grasping forceps may be in the form of a rongeur which locates the teeth inwardly of the rim on the jaws so that a barrier is formed between the teeth and the edge of the rim. This barrier serves to push the dura or vessel, for example, away from the teeth when the jaws of the rongeur are closed, thereby assuring that the dura or vessel will not be captured in the closing jaws by the teeth.

In the further embodiment of this invention the barrier is formed by members such as spring wires or metal bands located at the front and sides of the jaws which are bulged outwardly to press against the dura or vessel during the closing action of the jaws. Alternatively, the barrier may be located completely around the outer surface of each jaw to thereby extend outwardly of the jaws and push the dura or vessel away from the closing jaws.

A BRIEF DESCRIPTION OF THE DRAWINGS

FIG. 1 is a side elevational view of a grasping forceps in the form of a rongeur in accordance with one embodiment of this invention;

FIG. 2 is an enlarged side elevational view of the rongeur jaws shown in FIG. 1;

FIG. 3 is a fragmental cross-sectional view showing a portion of a jaw from the rongeur of FIGS. 1–2;

FIG. 4 is a fragmental bottom plan view of a rongeur jaw in the embodiment of FIGS. 1–3;

DETAILED DESCRIPTION

Figure 5:
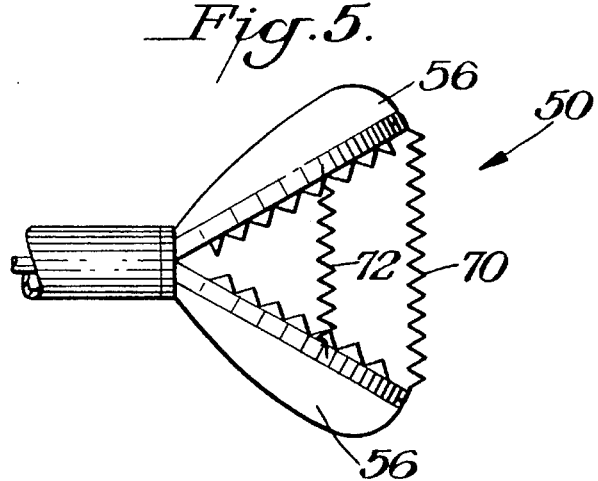
FIG. 5 is a side elevational view of another embodiment of this invention showing the rongeur jaws in an open condition.

Grasping forceps generally include a pair of coacting jaws having teeth for grasping material. A rongeur is a heavy duty forceps for removing small pieces of bone or tough tissue. The present invention may apply to various forms of grasping forceps but will be particularly described with respect to a rongeur.

FIGS. 1–4 illustrate a practice of this invention wherein the grasping forceps in the form of a rongeur 50 is shown which is of generally known construction in that it includes an outer tube 52 with inner telescopic member 54 movably disposed in outer tube 52. Member 54 terminates in a pair of jaws 56. The jaws 56 are selectively moved to an open and closed position by actuating scissor type handle assembly 58 in a known manner. Jaws 56 include teeth 60 which function to sever tissue and trap the severed tissue and other materials such as disc materials or fragments captured between the closed jaws. After the material is captured between the closed jaws the instrument or rongeur 50 is then removed.

When the handles of scissors assembly 58 are squeezed together or moved apart the jaw operating assembly 54 functions to selectively open and close the jaws.

With conventional rongeurs the teeth are disposed at the outer edge of the jaws. This leads to the problem in discectomy that during the closing action structure such as a portion of the dura or vessel might have entered the space between the jaws. The structure would thus be injured from the sets of teeth being closed together. The present invention minimizes this possibility by spacing the teeth inwardly from the outer edge 62 of each jaw 56. This is best illustrated in FIGS. 3 and 4.

Teeth 60 are preferably spaced inwardly from outer edge 62 by a sufficient distance such that when the jaws 56 of the rongeur 50 are opened to their maximum the teeth 60 are recessed enough so that they do not come into contact with the structure in danger.

As shown in FIGS. 3–4, a barrier or toothless rim 64 is thus located between the teeth 60 and the outer edge 62. This toothless rim 64 pushes the dura away from the teeth 60 of the rongeur instrument 50. As a result, the teeth can not reach the dura. During the closing action by the dura being pushed away from the teeth 60 there is less likelihood that the dura can be captured in the closing jaws 56, 56 and thereby injured.

Figure 7:
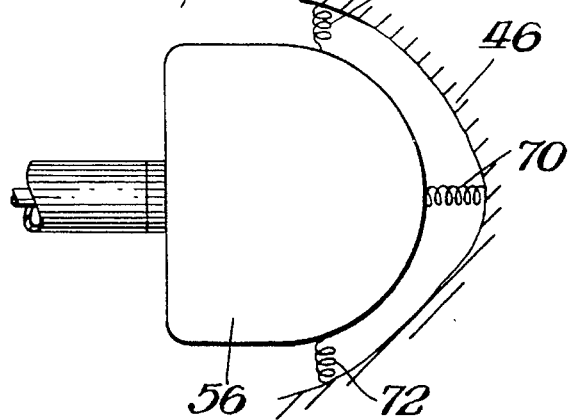
FIG. 7 is a top plan view of the rongeur shown in FIG. 6.
Figure 6:
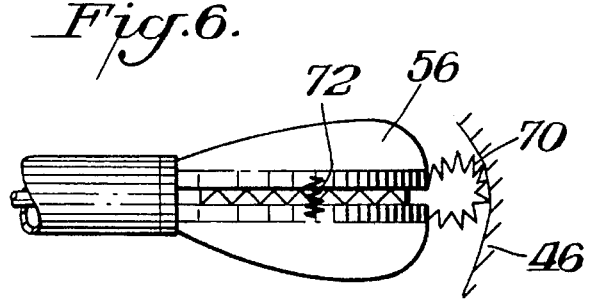
FIG. 6 is a side elevational view of the rongeur of FIG. 5 with the jaws in the closed position.

FIGS. 5–7 show another embodiment of this invention wherein the rongeur 50 includes the same structure of closeable jaws 56 and teeth 60. In this embodiment, however, rather than recessing the teeth to form the safety barrier a barrier is formed by structural elements secured to the outside of the jaws interconnecting the pair of jaws. These structural elements may take any suitable form such as springs, wires or metal bands. In the illustrated embodiment the structural elements comprise a spring 70 interconnecting jaws 56, 56 at the distal end of the jaws while a spring 72 is mounted at the sides of the jaws interconnecting the jaws. As best illustrated in FIG. 5 when the jaws are in the open condition illustrated in FIG. 5 the springs are stretched so as not to interfere with the forward movement of the jaws to the desired site. As best shown in FIGS. 6–7, as the jaws close the springs 70, 72 bow outwardly and press against the structure such as dura 46 to assure that the structure will not be captured in the closing jaws.

Figure 9:
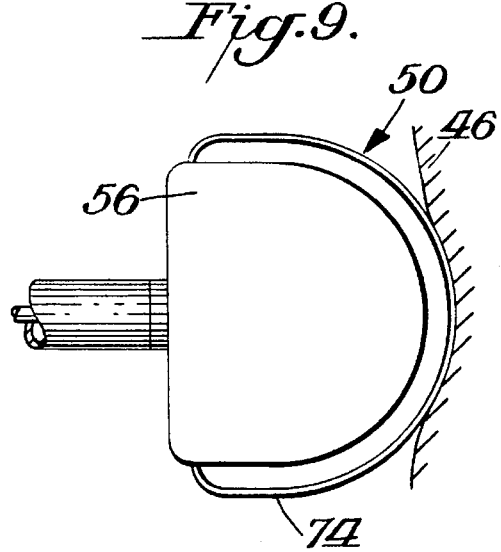
FIG. 9 is a top plan view of the rongeur shown in FIG. 8.
Figure 8:
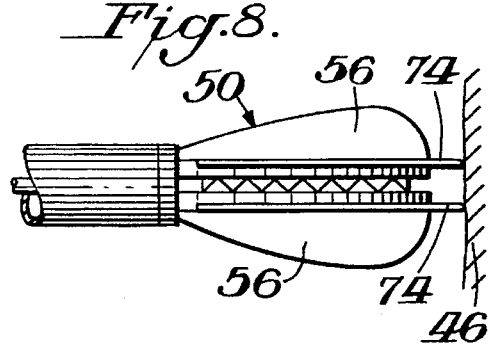
FIG. 8 is a side elevational view of still yet another embodiment of this invention with the jaws in the closed position.

FIG. 8–9 show a variation wherein each jaw 56 is provided with a barrier in the form of a wire guide 74 mounted to its respective jaw peripherally around its jaw.

When the jaws are in the open condition the rongeur 50 may be moved toward the dura. As shown in FIGS. 8–9, during the closing action the barriers or wire guards 74 tend to push against the dura thereby moving the dura or other structure away from the closing jaws.

The embodiments of FIGS. 5–7 and 8–9 may have the teeth arranged on the jaws in a conventional manner where there is no barrier formed by recessing the teeth. Alternatively, the teeth may also be recessed in the manner of FIGS. 1–4 to add further assurance of preventing injury to structures such as the dura or vessels. It is to be understood that various features shown in any one embodiment may be used in other embodiments within the practice of this invention.

The present invention may be practiced with various types of grasping forceps having at least one jaw with teeth, particularly forceps having double action jaws with teeth. The forceps may be used for various purposes such as for grasping stones or stone fragments or as biopsy forceps.

What is claimed is:

1. In a grasping forceps having a pair of jaws with teeth in at least one of the jaws and with a jaw actuating assembly for controlling the opening and closing movement of the jaws, the improvement being in that each of said jaws includes a barrier at its outer edge for pushing structure away from said teeth during the closing action of said jaws, each set of said teeth being mounted in a row to its respective jaw about the periphery of and spaced inwardly of said outer edge, a peripheral rim being located between said outer edge and said teeth to form said barrier, said rims of said jaws being spaced from each other when said jaws are in their fully closed position to prevent said rims from contacting each other and thereby damaging structure when said jaws are in said fully closed position, and all of said teeth being disposed inwardly of said outer edge and not extending outwardly beyond said outer edge when said jaws are in their fully open position to prevent said teeth from contacting and damaging structure when said jaws are in said fully open position.

2. The forceps of claim 1 wherein each of said jaws includes teeth spaced inwardly from its outer edge, and said jaws being double action jaws.

3. The forceps of claim 1 wherein at least one guide member is mounted at the outer edge of said jaws.

4. The forceps of claim 3 wherein said at least one guide member comprises a guide member interconnecting said jaws at the distal end of said jaws.

5. The forceps of claim 4 wherein said at least one guide member further comprises a guide member interconnecting said jaws at said outer edge of said jaws inwardly of said distal end at opposite sides of said jaws.

6. The forceps of claim 5 wherein said guide members are springs.

7. The forceps of claim 4 wherein said at least one guide member comprises a guide member interconnecting said jaws inwardly of the distal end of said jaws at opposite sides of said jaws.

8. The forceps of claim 3 wherein said at least one guide member comprises a guide member secured to and outwardly of each of said jaws.

9. The forceps of claim 8 wherein each of said guide member extends peripherally around each of said jaws.

10. The forceps of claim 1 wherein said forceps is a rongeur.

11. In a surgical method using a grasping forceps which includes double action jaws having teeth on each jaw for confining material therebetween when the jaws are closed, the improvement being in providing a barrier on the outer edge of each jaw, utilizing the barrier to push structure away from the teeth during the closing action of the jaws, the teeth being mounted in a row about the periphery of and spaced inwardly of the outer edge of each jaw to create a peripheral rim between the teeth and the outer edge, the rim being utilized as the barrier, spacing the rims from each other when the laws are manipulated to their fully closed position to prevent the rims from contacting each other and thereby damaging structure when the jaws are in their fully closed position, and maintaining all of the teeth inwardly of the rims without extending outwardly beyond the rims when the jaws are in their fully open position to prevent the teeth from contacting and damaging structure when the jaws are in their fully open position.

12. The method of claim 11 wherein at least one guide member is connected to each of the jaws, and the guide member pushes against the structure.

13. The method of claim 12 wherein a guide member interconnects the jaws at the distal end of the jaws and guide members interconnect the jaws on each side of the jaws inwardly of the distal end, and the guide members bowing outwardly during the closing action of the jaws to push against the structure.

14. The method of claim 12 wherein a guide member is mounted on each jaw peripherally around its jaw and outwardly of its jaw to push against the structure.

* * * * *